United States Patent
Cotugno et al.

(10) Patent No.: US 9,908,998 B2
(45) Date of Patent: Mar. 6, 2018

(54) CLASS OF RUBBER PRODUCT ANTI-AGING AGENTS

(71) Applicant: BRIDGESTONE CORPORATION, Tokyo (JP)

(72) Inventors: Salvatore Cotugno, Rome (IT); Ludovica Caliano, Pomezia (IT); John House, Rome (IT); Giovanna Mancini, Rome (IT); Alessandro Mauceri, Rome (IT); Luisa Giansanti, Rome (IT)

(73) Assignee: BRIDGESTONE CORPORATION, Tokyo (JP)

( * ) Notice: Subject to any disclaimer, the term of this patent is extended or adjusted under 35 U.S.C. 154(b) by 1 day.

(21) Appl. No.: 15/032,839

(22) PCT Filed: Oct. 29, 2014

(86) PCT No.: PCT/IB2014/065693
§ 371 (c)(1),
(2) Date: Apr. 28, 2016

(87) PCT Pub. No.: WO2015/063703
PCT Pub. Date: May 7, 2015

(65) Prior Publication Data
US 2016/0251502 A1    Sep. 1, 2016

(30) Foreign Application Priority Data

Oct. 29, 2013 (IT) .............................. RM2013A0596
Oct. 29, 2013 (IT) .............................. RM2013A0597

(51) Int. Cl.
| | | |
|---|---|---|
| *C08L 9/00* | (2006.01) | |
| *B60C 1/00* | (2006.01) | |
| *C07C 43/23* | (2006.01) | |
| *C08K 5/13* | (2006.01) | |

(52) U.S. Cl.
CPC *C08L 9/00* (2013.01); *B60C 1/00* (2013.01); *C07C 43/23* (2013.01); *C08K 5/13* (2013.01)

(58) Field of Classification Search
CPC .. C08L 9/00; B60C 1/00; C07C 43/23; C08K 5/13
USPC ........................................................ 524/323
See application file for complete search history.

(56) References Cited

U.S. PATENT DOCUMENTS

| | | |
|---|---|---|
| 4,435,477 A | 3/1984 | Davis |
| 2007/0191627 A1 | 8/2007 | Szekeres et al. |
| 2013/0203688 A1 | 8/2013 | Barbeau et al. |

FOREIGN PATENT DOCUMENTS

| | | | |
|---|---|---|---|
| GB | 699180 A | 11/1953 | |
| WO | WO 2012021983 A1 * | 2/2012 | ........... A61K 31/085 |

OTHER PUBLICATIONS

L. K. Fazlieva, et al., "Stabilizing agent for isoprene rubber and thermoplastic composition based on it", XP002727182, Chemical Abstracts Service.
L. K. Fazlieva, et al., "Stabilizing agent for isoprene rubber and thermoplastic composition based on it", XP009179075, Zhurnal Prikladnoi Khimii, pp. 1404-1406, vol. 69. No. 8.
International Search Report for PCT/IB2014/065693 dated Jan. 30, 2015 [PCT/ISA/210].
Written Opinion for PCT/IB2014/065693 dated Jan. 30, 2015 [PCT/ISA/237].

* cited by examiner

*Primary Examiner* — Angela C Scott
(74) *Attorney, Agent, or Firm* — Sughrue Mion, PLLC

(57) ABSTRACT

Use, as an anti-aging agent in polymer compounds, stilbene family compound of general formula (I): wherein the substitutes are selected from the following five combinations: a) $R^1$, $R^3$ and $R^5$ are OH; $R^2$, $R^4$ and $R^6$ are H; b) $R^1$ and $R^4$ are $OCH_3$; $R^2$ and $R^5$ are OH; $R^3$ and $R^6$ are H; c) $R^1$ and $R^4$ are OH; $R^2$ and $R^5$ are $OC(CH_3)_3$; $R^3$ and $R^6$ are H; d) $R^1$ and $R^4$ are $OCH_3$; $R^2$ and $R^5$ are OH; $R^3$ and $R^6$ are $C(CH_3)_3$; e) $R^1$ and $R^4$ are $OC(CH_3)_3$; $R^2$ and $R^5$ are OH; $R^3$ and $R^6$ are H.

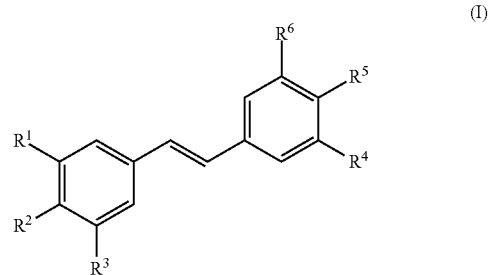

(I)

4 Claims, No Drawings

CLASS OF RUBBER PRODUCT ANTI-AGING AGENTS

CROSS REFERENCE TO RELATED APPLICATIONS

This application is a National Stage of International Application No. PCT/IB2014/065693 filed Oct. 29, 2014, claiming priority based on Italian Patent Application Nos. RM2013A000596 filed Oct. 29, 2013 and RM2013A000597 filed Oct. 29, 2013, the contents of all of which are incorporated herein by reference in their entirety.

TECHNICAL FIELD

The present invention relates to a new class of rubber product anti-aging agents.

More specifically, the present invention may be used to advantage in tyres, to which the following description refers purely by way of example.

BACKGROUND ART

As is known, the rubber compounds used to make tyre parts comprise anti-aging agents to prevent deterioration of the rubber caused by the polymer base reacting with oxygen and/or ozone.

Anti-aging agents are materials added to compounds susceptible to oxidation, such as rubber, to prevent or slow down oxidation processes (by themselves becoming oxidized). In other words, anti-aging agents are materials capable of reacting with atmospheric agents and so preventing the latter from reacting with the polymer base.

The anti-aging agent concentration in the compound depends on the degree of exposure to the atmosphere, and on the temperature and mechanical stress conditions to which the tyre part made from the compound is subjected.

The most commonly used anti-aging agents form part of the paraphenylenediamine (PPD) family, such as N-1,3-dimethylbutyl-N'-phenyl-paraphenylenediamine (6PPD) and N,N'-diphenyl-p-phenylenediamine (DPPD), or may be phenol derivatives, such as 2,6-di-tert-butyl-4-methylphenol (BHT), or form part of the vitamin E family, such as α-tocopherol, α-tocotrienol, γ-tocopherol and γ-tocotrienol, or the quinoline family, such as poly(1,2-dihydro-2,2,4-trimethylquinoline) (TMQ).

Research by the Applicant has uncovered a new class of anti-aging agents which, in polymer compounds, and particularly rubber compounds, may be used as a valid alternative to known anti-aging agents.

DISCLOSURE OF INVENTION

One object of the present invention is the use, as an anti-aging agent in polymer compounds, of a stilbene family compound of general formula (I):

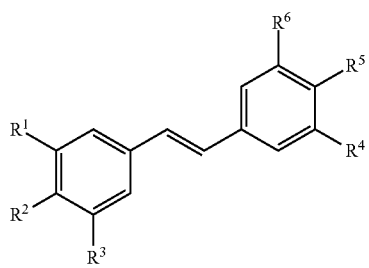

wherein the substitutes are selected from the following five combinations:
a) $R^1$, $R^3$ and $R^5$ are OH; $R^2$, $R^4$ and $R^6$ are H;
b) $R^1$ and $R^4$ are $OCH_3$; $R^2$ and $R^5$ are OH; $R^3$ and $R^6$ are H;
c) $R^1$ and $R^4$ are OH; $R^2$ and $R^5$ are $OC(CH_3)_3$; $R^3$ and $R^6$ are H;
d) $R^1$ and $R^4$ are $OCH_3$; $R^2$ and $R^5$ are OH; $R^3$ and $R^6$ are $C(CH_3)_3$;
e) $R^1$ and $R^4$ are $OC(CH_3)_3$; $R^2$ and $R^5$ are OH; $R^3$ and $R^6$ are H.

The polymer compounds are preferably rubber compounds.

Another object of the present invention is a polymer compound, preferably a rubber compound comprising at least one polymer base, a curing system, and an anti-aging agent selected from the above five compounds.

Another object of the present invention is a tyre part made from a rubber compound comprising an anti-aging agent selected from the above five compounds.

Another object of the present invention is a tyre comprising a part as defined above.

Another object of the present invention is a material of general formula (I):

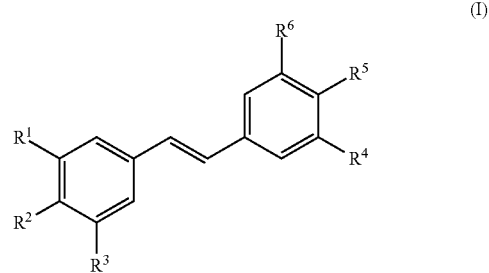

wherein $R^1$ and $R^4$ are OH; $R^2$ and $R^5$ are $OC(CH_3)_3$; $R^3$ and $R^6$ are H.

For the sake of clarity, the following are five anti-aging agents in accordance with the present invention.

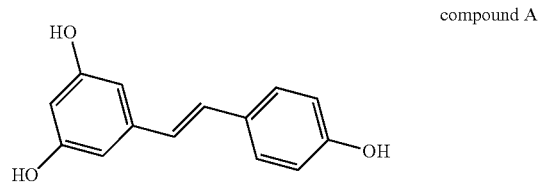

compound A

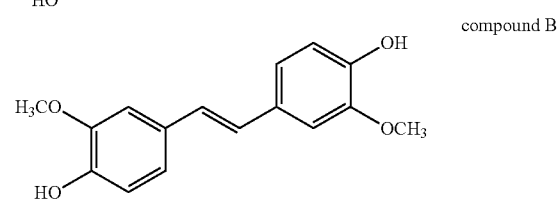

compound B

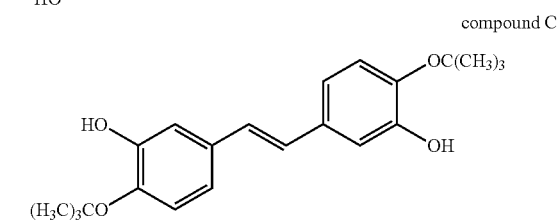

compound C

Being a new compound, compound C, in addition to being claimed for its use as an anti-aging agent, is also claimed as a compound in its own right. The synthesis schematic as a whole is shown below:

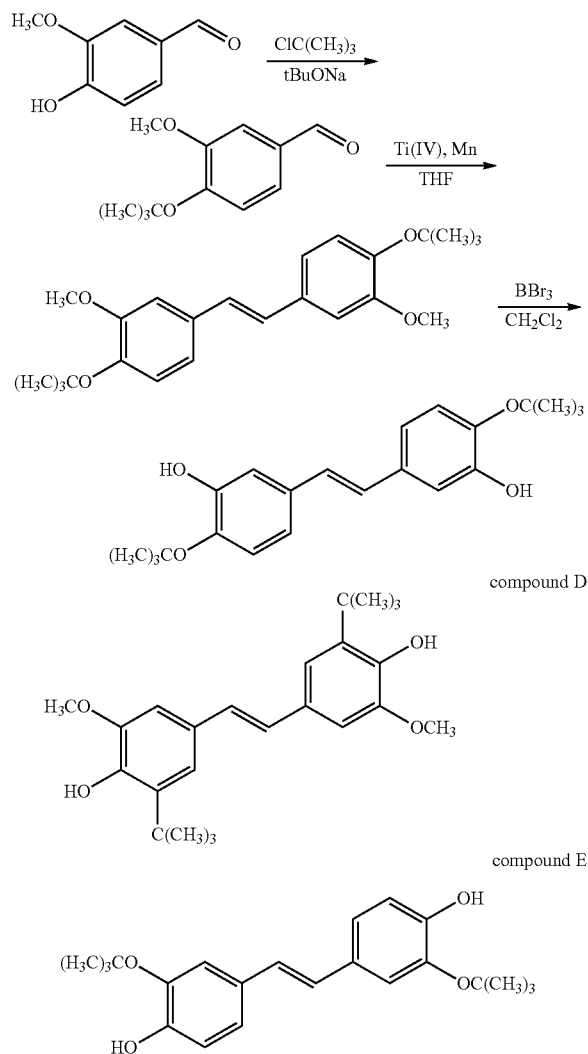

For a clearer understanding of the present invention, the following are a number of embodiments purely by way of non-limiting examples.

BEST MODE FOR CARRYING OUT THE INVENTION

EXAMPLES

The Applicant has tested the rubber anti-aging performance of two compounds (A and B) of general formula (I). The structural formulas of compounds A and B are shown below.

—Anti-aging Testing of Material A and B—

To test the rubber anti-aging performance of the materials according to the present invention, a gas chromatography-based test method was prepared, in which a model compound (MC), in this case cumene, is substituted for the elastomer. The oxidation-reducing phenomenon of the cumene was activated by a radical initiator (azobisisobutyronitrile) and evaluated at a controlled temperature of 140° C. in the presence of oxygen at greater than atmospheric pressure.

The composition used for the above tests was cumene 3 ml; n-decane 1.5 ml; azobisisobutyronitrile 20 mg.

After producing the conditions indicated above, a sample of the mixture was taken periodically to determine, by gas chromatography, the amount of cumene consumed by reaction with oxygen.

The above oxidation tests were conducted both with and without an anti-aging agent.

More specifically, five oxidation tests were conducted: with no anti-aging agent; with $2.46*10^{-2}$ m of 6PPD; with $2.46*10^{-2}$ m of TMQ; with $2.46*10^{-2}$ m of material A; and with $2.46*10^{-2}$ m of material B.

The oxidation tests were conducted in the conditions described above. For each oxidation test, a 0.1 ml sample of the mixture was taken 0, 2, 4, 6 and 8 hours after the above test conditions were produced. And each sample was analysed by gas chromatography to determine the amount of cumene remaining after the oxidation reaction.

Table I shows the amounts of cumene detected in the oxidation tests on the basis of the anti-aging agent used and the sampling time interval. The cumene quantities are expressed as residual percentages of the initial amount of cumene. The measurement was made possible using n-decane as a reference standard.

TABLE I

|  | 0 h | 2 h | 4 h | 6 h | 8 h |
| --- | --- | --- | --- | --- | --- |
| No anti-aging agent | 100 | 75 | 60 | 55 | 50 |
| 6PPD | 100 | 100 | 97 | 95 | 92 |
| TMQ | 100 | 100 | 96 | 94 | 92 |
| Compound A | 100 | 97 | 98 | 95 | 90 |
| Compound B | 100 | 100 | 100 | 99 | 93 |

The higher the residual cumene percentage is, the greater the anti-oxidizing capacity of the compound is.

The Table I figures show the potential of the anti-aging agents considered in the present invention as valid, promising alternatives to commonly used anti-aging agents.

In fact, the cumene values for compounds comprising anti-aging agents in accordance with the present invention are comparable with, if not higher than, those of compounds comprising commonly used rubber compound anti-aging agents.

It is important to note that oxidation testing was conducted at high temperature to determine the anti-oxidizing and anti-ozonizing capacity of the compounds according to the present invention in especially severe conditions.

To further confirm the effectiveness of the anti-aging agents according to the present invention, tests were conducted of compounds with compositions characteristic of specific tyre parts.

Three rubber compounds (I-III) were produced with the compositions in phr shown in Table II.

TABLE II

| COMPOUND | I | II | III |
| --- | --- | --- | --- |
| BR |  | 60 |  |
| NR |  | 40 |  |
| CB |  | 30 |  |
| SULPHUR |  | 1.5 |  |

TABLE II-continued

| COMPOUND | I | II | III |
|---|---|---|---|
| TBBS | | 0.8 | |
| STEARIC ACID | | 2 | |
| ZnO | | 3 | |
| 6PPD | — | 1.5 | — |
| Compound B | — | — | 1.5 |

Compounds I-III were produced using the standard method described below:

(1st Mixing Step)

Prior to mixing, a 230-270-litre, tangential-rotor mixer was loaded with the polymer base, carbon black, and the anti-aging agent, to a fill factor of 66-72%.

The mixer was operated at a speed of 40-60 rpm, and the resulting mixture unloaded on reaching a temperature of 145-165° C.

(2nd Mixing Step)

The mixture from the first step was mixed again in the mixer operated at a speed of 40-60 rpm, and was unloaded on reaching a temperature of 130-150° C.

(3rd Mixing Step)

Stearic acid and the curing system, comprising sulphur, accelerants and zinc oxide, were added to the mixture from the second step to a fill factor of 63-67%.

The mixer was operated at a speed of 20-40 rpm, and the resulting mixture unloaded on reaching a temperature of 100-110° C.

The compounds in Table II were tested to determine their mechanical properties.

The mechanical properties were measured as per ASTM Standard D412C.

More specifically, the M300 modulus related property was measured.

The M300 modulus was measured on samples both before and (3 and 6 days) after an aging process in which the samples were kept in an oven at 70° C. as per ISO Standard 188.

Table III shows the M300 modulus results of the above samples.

To show more clearly the advantages of the compound according to the present invention, the test results in Table III are indexed with respect to those of the individual compounds prior to aging.

TABLE III

| Compound | I | II | III |
|---|---|---|---|
| 0 days | 100 | 100 | 100 |
| 3 days | 65 | 74 | 77 |
| 6 days | 27 | 74 | 74 |

As shown by the figures in Table III, using the anti-aging agents according to the present invention in the compound ensures the mechanical properties of the compound are maintained to a degree comparable with known anti-aging agents.

The invention claimed is:

1. A polymer composition comprising at least one polymer base, a curing system, and an anti-aging agent; wherein said anti-aging agent is a stilbene family compound of general formula (I):

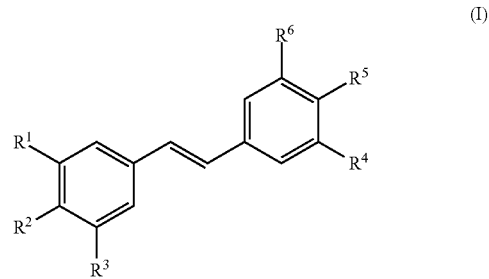

wherein the substitutes are selected from the following five combinations:
a) $R^1$, $R^3$ and $R^5$ are OH; $R^2$, $R^4$ and $R^6$ are H;
b) $R^1$ and $R^4$ are $OCH_3$; $R^2$ and $R^5$ are OH; $R^3$ and $R^6$ are H;
c) $R^1$ and $R^4$ are OH; $R^2$ and $R^5$ are $OC(CH_3)_3$; $R^3$ and $R^6$ are H;
d) $R^1$ and $R^4$ are $OCH_3$; $R^2$ and $R^5$ are OH; $R^3$ and $R^6$ are $C(CH_3)_3$; and
e) $R^1$ and $R^4$ are $OC(CH_3)_3$; $R^2$ and $R^5$ are OH; $R^3$ and $R^6$ are H.

2. The polymer composition as claimed in claim 1, wherein said composition is a rubber composition.

3. A tire part, wherein said tire part is made from the composition as claimed in claim 2.

4. A tire, comprising the part as claimed in claim 3.

* * * * *